(12) United States Patent
Lengsfeld et al.

(10) Patent No.: US 7,919,592 B2
(45) Date of Patent: Apr. 5, 2011

(54) METHOD FOR SEPARATING OFF VIRUSES FROM A PROTEIN SOLUTION BY MEANS OF NANOFILTRATION

(75) Inventors: Thomas Lengsfeld, Marburg (DE); Heinrich Schneider, Lahntal (DE)

(73) Assignee: ZLB Behring GmbH, Marburg (DE)

( * ) Notice: Subject to any disclaimer, the term of this patent is extended or adjusted under 35 U.S.C. 154(b) by 0 days.

(21) Appl. No.: 10/386,486

(22) Filed: Mar. 13, 2003

(65) Prior Publication Data

US 2003/0232969 A1    Dec. 18, 2003

(30) Foreign Application Priority Data

Mar. 15, 2002   (DE) .................................. 102 11 632

(51) Int. Cl.
*C07K 14/775* (2006.01)
*A61K 38/00* (2006.01)

(52) U.S. Cl. ............................................ 530/383; 514/2

(58) Field of Classification Search .................. 435/6, 2, 435/13; 530/412, 414, 417, 344, 355, 361, 530/364, 368–369, 380–386
See application file for complete search history.

(56) References Cited

U.S. PATENT DOCUMENTS

| | | | | |
|---|---|---|---|---|
| 6,447,774 B1 * | 9/2002 | Metzner et al. | ............ | 424/94.64 |
| 6,867,285 B2 * | 3/2005 | Takahashi et al. | ............ | 530/382 |
| 6,967,239 B1 * | 11/2005 | Chtourou et al. | ............ | 530/383 |
| 2001/0033837 A1 | 10/2001 | Metzner et al. | | |
| 2001/0051154 A1 | 12/2001 | Roemisch et al. | | |
| 2003/0133928 A1 | 7/2003 | Metzner et al. | | |

FOREIGN PATENT DOCUMENTS

| | | | |
|---|---|---|---|
| EP | 1 136 084 A1 | | 9/2001 |
| EP | 1 153 608 A1 | | 11/2001 |
| WO | WO 99/19343 | | 4/1999 |
| WO | WO 99/23111 | | 5/1999 |
| WO | WO 99/64441 | * | 12/1999 |
| WO | WO 00/29041 | * | 5/2000 |
| WO | WO 01/45719 A1 | * | 6/2001 |

OTHER PUBLICATIONS

Troccoli et al. Removal of viruses from Human intravenous immune globulin by 35 nm nanofiltration. Biologicals, 1998, vol. 26, 321-329.*
Chang et al. Surface denaturation of proteins during freezing and its inhibition by surfactants. Journal of Pharmaceutical Sciences, Dec. 1996, vol. 85, No. 12, 1325-1330.*
Peter L. Roberts, *Value of Virus Filtration as a Method for Improving the Safety of Plasma Products*, Vox Sang 69: 82-83 (1995).
European Search Report dated Jul. 30, 2003.

* cited by examiner

*Primary Examiner* — Anand U Desai
(74) *Attorney, Agent, or Firm* — Finnegan, Henderson, Farabow, Garrett & Dunner, L.L.P.

(57) ABSTRACT

A method for separating off viruses from a protein solution by nanofiltration, comprising adding to the protein solution at least one ingredient chosen from chaotropic substances chosen from arginine, guanidine, citrulline, urea and derivatives thereof and salts thereof, and compounds chosen from polyethoxysorbitan esters and derivatives thereof, prior to the nanofiltration, in order to decrease or prevent aggregation of the protein molecules, and then filtering the solution through a filter having a pore size ranging from 15 nm to less than 35 nm.

5 Claims, 2 Drawing Sheets

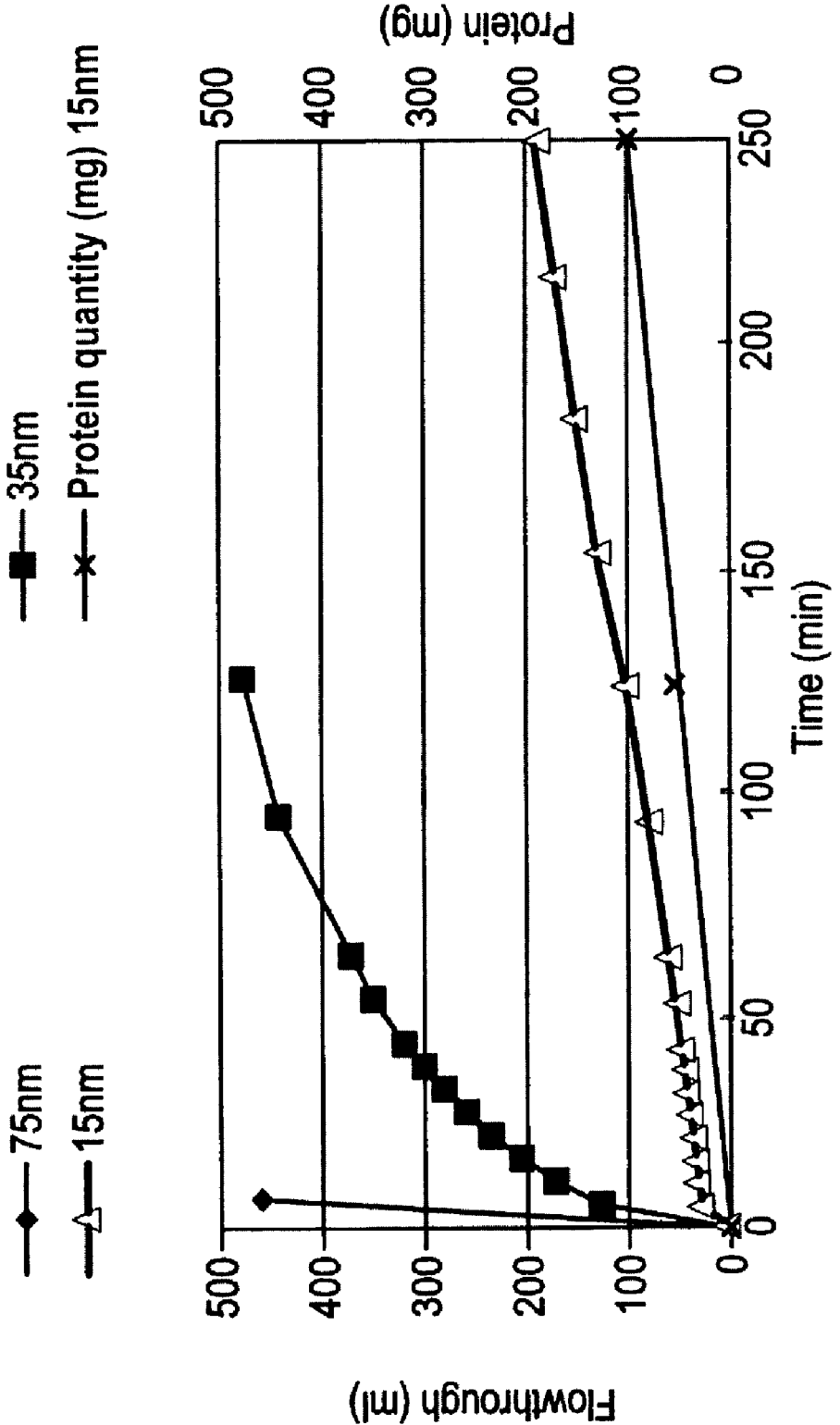

Figure 1B:
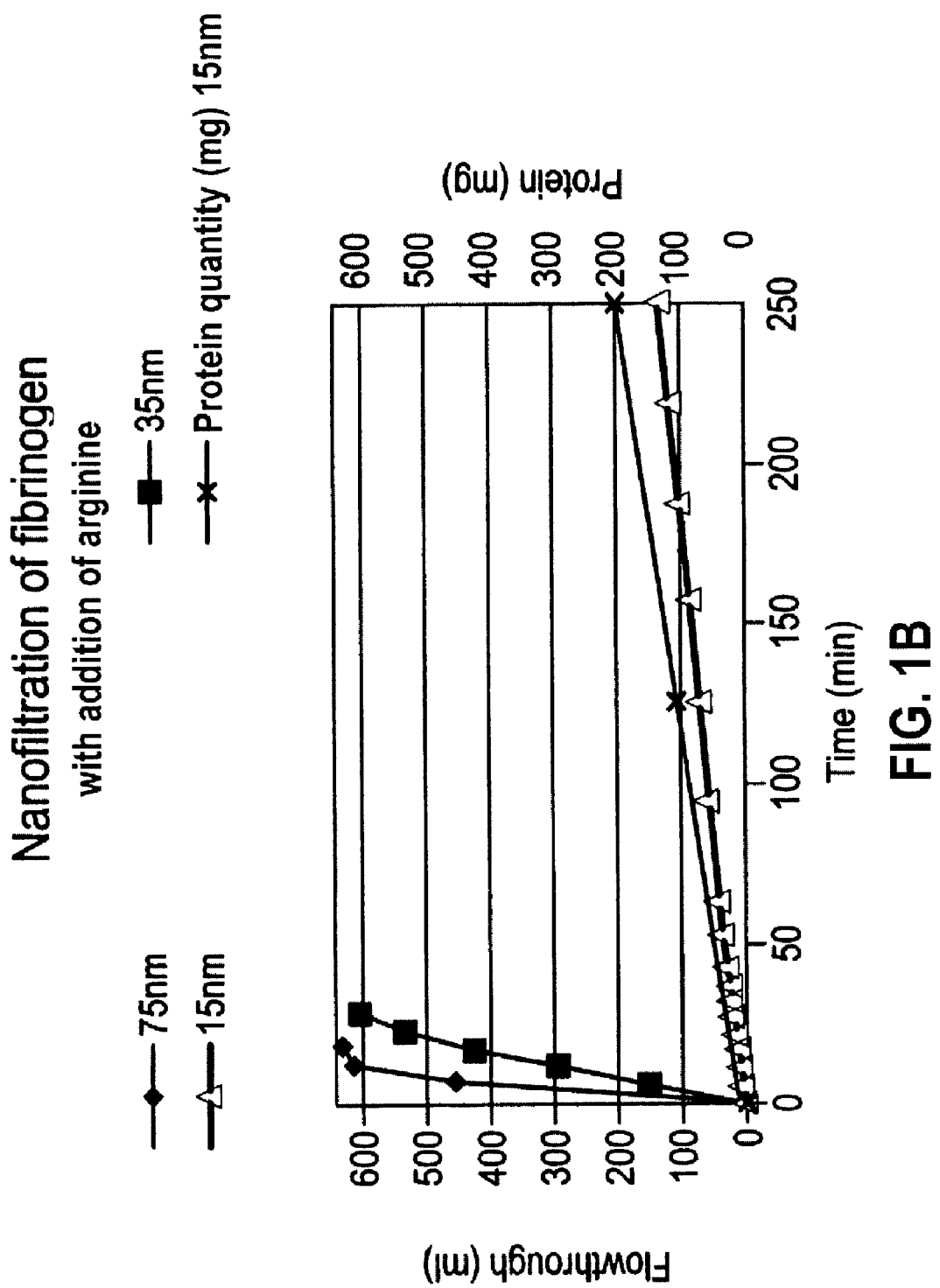

METHOD FOR SEPARATING OFF VIRUSES FROM A PROTEIN SOLUTION BY MEANS OF NANOFILTRATION

The invention relates to the nanofiltration of protein solutions, by means of which it is possible to separate off viruses virtually completely.

The cost of a nanofiltration process is determined by the efficacy of the flow rate/transport of material across a membrane. In other words, the filter area needed to process the product is a key factor. The rate at which a liquid will flow through a membrane filter (volume filtered per unit of time) is a function of filtration area, differential pressure, and fluid viscosity:

$$Q = C_1 \frac{A \times P}{V}$$

Q=flow rate
A=filtration area
P=differential pressure
V=viscosity of the fluid
$C_1$=resistance of the fluid flow of the filtration medium The size and quantity of particles or molecules trapped on the filter surface affect the amount of open pore volume of the filter and therefore the flow. The more contaminants and aggregates are present, the less the efficacy of the filtration process (Levy and Leahy, 1991). Also building of a polarization gel of proteins on the surface of the membrane, which depends upon the physicochemical environment, may affect the process (tangential flow systems).

In the case of small protein molecules, nanofiltration is a very effective method for removing viruses. In this connection, the pore size of the filter has to be smaller than the effective diameter of the virus which is to be removed. In addition, the temperature, the properties of the materials and the buffering conditions are of importance when carrying out a nanofiltration. Previous studies have already demonstrated that parvovirus can be reliably removed using filters having a pore diameter of 15 nm. Nanofiltration has also already been used for separating off hepatitis A virus and parvovirus from factor IX preparations, with filters such as VIRESOLVE® 70 (VIRESOLVE® tangential flow filtration module 70), PLANOVA® 15 N (PLANOVA® filter with a mean pore size of 15 nm) and PALL ULTIPOR™ DV20 (Pall Ultipor™ filter for size exclusion removal of viruses as small as 20 nm from biological solutions) having proved to be effective. In contrast, blood coagulation factor IX has a low molecular weight of 56 kDa and is therefore not retained by the membranes employed for the nanofiltration. However, large proteins, such as fibrinogen, von Willebrand factor and factor VIII, have thus far been regarded as being too big to be freed from viruses by filtering them through a nanofilter having a pore size of from 15 to 35 nm.

Fibrinogen is a 340 kDa hexameric ($a_2b_2g_2$) glycoprotein. The crystal structure of natural chick fibrinogen shows a length of 46 nm. Electron microscopic measurements have demonstrated that fibrinogen has a three-node structure, with a length of 47.5 nm and a node size of 6.5 nm. In addition, hydration leads to the fibrinogen molecule increasing in size. For this reason, filtration methods for fibrinogen have thus far only been described for a filter pore size of 35 nm. These methods suffer from the disadvantage that, when the pore size is 35 nm, relatively small, nonenveloped viruses such as hepatitis A virus and parvovirus cannot be removed. Even though nanofilters having a pore size of 20 nm or less, which could be used for removing hepatitis A viruses or parvoviruses as well, are available, it has not been possible, up to now, to use these filters when purifying fibrinogen since the fibrinogen molecule is regarded as being too bulky for this pore size (Roberts, P., Vox Sang, 1995; 69: 82-83).

Since, however, nanofiltration is a mild method for removing viruses from protein solutions, and the biological activity of the proteins can be fully preserved in this connection, the object presented itself of developing a method for removing viruses from protein solutions by means of nanofiltration, which method can be used to make even large-volume protein molecules available for nanofiltration.

This object can be achieved by a method comprising adding to a protein solution at least one ingredient chosen from chaotropic substances chosen from arginine, guanidine, citrulline, urea, and derivatives thereof and salts thereof and compounds chosen from polyethoxysorbitan esters and derivatives thereof prior to the nanofiltration, in order to decrease or prevent aggregation of the protein molecules, or the formation of a hydrate sheath around the molecules. The solution is then filtered through a filter having a pore size ranging from 15 nm to less than 35 nm, such as from 15 nm to 25 nm. The polyethoxysorbitan esters and derivatives thereof are, for example, chosen from non-ionic surfactants.

The method is suitable for separating off viruses from a fibrinogen solution or from a solution of a blood coagulation factor, for example, factor VIII.

The method can be carried out at room temperature, so that thermal stress can be avoided; and the loss of the biological activity of the protein molecules, which is associated therewith, can also be avoided. In this way, it is possible for proteins having molecular weights of from 200 to 340 kDa to be freed from viruses using a pore size ranging from 15 nm to less than 35 nm, such as from 15 nm to 25 nm. For example, members of the parvovirus family, which have a globular particle size of from 18 to 26 nm, and hepatitis A viruses, having a rod-shaped structure of from 6 to 17 nm in diameter and of about 48 nm in length, can be removed in this way.

In addition, the filtration method according to the invention can further comprise a conventional pasteurization, which can result in further viral depletion.

The nanofilters which are used for the method according to the invention are available commercially and can be purchased, for example, under the designations PALL ULTIPOR™ DV-15 and DV-20 (Pall Ultipor™ filter for size exclusion removal of viruses as small as 15 nm and 20 nm, respectively, from biological solutions), inter alia.

The present invention is further illustrated by the following comparative examples, without, however, being limiting in nature.

Filtration experiments were performed in a four step process mode. The filtration solution was first clarified by a 0.22 µm dead end filtration to remove macrosize particles. A 75 nm dead end filtration was performed to further remove the largest aggregates. Then, after a 35 nm cross flow filtration, the 15 nm filtration was performed under cross flow conditions. All filtration processes were performed at 37° C. and the protein concentration is below 5 mg/ml.

The filtration processes were investigated in regard to flow and protein transport.

The fibrinogen filtration was investigated with and without 6% arginine monohydrochloride added to the filtration solution (FIG. 1). The filtration flowthrough (ml) was measured at different times for filters with a pore size of 15 nm, 35 nm, and 75 nm, respectively. In addition, the global protein yield in the filtrate was measured at different times for the filter with a pore size of 15 nm (i.e., Protein quantity (mg) 15 nm).

The global protein yield in the filtrate can readily be determined by one of ordinary skill in the art using known techniques.

FIGS. 1A and 1B show nanofiltration of the fibrinogen solution with and without addition of arginine monohydrocholoride, respectively. In both figures, the flowthough increases as the pore size of the filter increases. It was found that arginine enhances the global protein yield in the filtrate even when the pore size of the filter is 15 nm. In FIG. 1A, without the addition of arginine, 100 mg protein was transferred across the 15 nm membrane in 250 minutes. However, in the presence of arginine, 200 mg protein was transferred across the 15 nm membrane in 250 minutes (FIG. 1B). Therefore, when arginine monohydrochloride is added, satisfactory quantities of fibrinogen filtrate can be obtained even when the pore size of the filter is 15 nm.

What is claimed is:

1. A method for separating off viruses from a protein solution by nanofiltration, comprising adding to the protein solution at least one ingredient chosen from chaotropic substances chosen from arginine, guanidine, citrulline, urea and derivatives thereof and salts thereof, and then filtering the protein solution through a filter having a pore size ranging from 15 nm to less than 35 nm, wherein the protein solution is a fibrinogen solution, wherein the pore size is less than the single particle size of the viruses, and wherein the fibrinogen passes through the filter and the filter retains the viruses.

2. The method according to claim 1, wherein said method is carried out at room temperature.

3. The method according to claim 1, further comprising a pasteurization.

4. The method according to claim 1, wherein the filter has a pore size ranging from 15 nm to 25 nm.

5. The method according to claim 1, wherein the chaotropic substance is arginine or a salt thereof.

* * * * *